Figure 1:
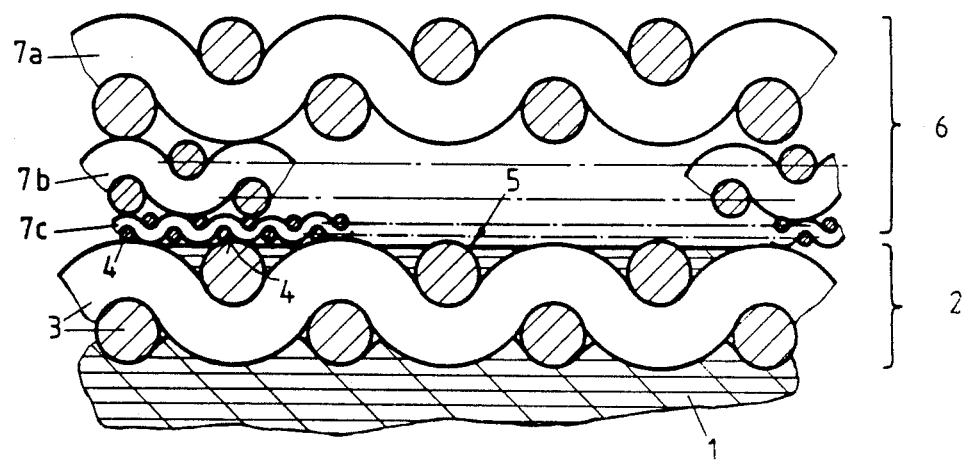

United States Patent [19]

Frey et al.

[11] Patent Number: 4,978,355
[45] Date of Patent: Dec. 18, 1990

[54] PLASTIC BONE IMPLANT HAVING A REINFORCED CONTACT SURFACE

[75] Inventors: Otto Frey; Manfred Semlitsch; Heinz Weber, all of Winterthur, Switzerland

[73] Assignee: Sulzer Brothers Limited, Winterthur, Switzerland

[21] Appl. No.: 816,340

[22] Filed: Jan. 6, 1986

[30] Foreign Application Priority Data

Jan. 25, 1985 [CH] Switzerland ............ 328/85

[51] Int. Cl.⁵ .............................................. A61F 2/30
[52] U.S. Cl. ........................................................ 623/16
[58] Field of Search ............................... 623/16–23, 623/11

[56] References Cited

U.S. PATENT DOCUMENTS 3,906,550 9/1975 Rostoker et al. ................ 623/18
4,195,368 4/1980 Patrichi ............................. 623/18
4,479,271 10/1984 Bolesky et al. ................... 623/20
4,542,539 9/1985 Rowe, Jr. et al. ................. 623/16
4,570,271 2/1986 Sump ................................ 623/18

FOREIGN PATENT DOCUMENTS 0038902 11/1981 European Pat. Off. ............. 623/23
2059267 4/1981 United Kingdom ................ 623/23

Primary Examiner—David J. Isabella
Attorney, Agent, or Firm—Kenyon & Kenyon

[57] ABSTRACT

A metal grid is embedded in the contact surface of a plastic implant in order to increase the wear resistance of the plastic implant. The ridge dimensions of the metal grid are chosen so that the elasticity of the plastic implant is not unduly reduced. An additional anchoring surface formed of layers of porous metal may be secured to the embedded grid to provide a surface into which bone tissue may grow in a cementless anchorage.

5 Claims, 2 Drawing Sheets

PLASTIC BONE IMPLANT HAVING A REINFORCED CONTACT SURFACE

This invention relates to a bone implant. More particularly, this invention relates to a plastic bone implant having a reinforced contact surface Heretofore, various types of implants have been known for implanting in the human body. In some cases, the implants have been made of plastic and have been used, for example as a hip joint socket. In these cases, the surfaces of the plastic hip joint sockets have been provided, at least partially, with a structure to promote a cement-free anchorage.

It has been found in practice that plastic implants, for example, made of polyethylene, undergo considerable wear in a cement-free anchorage due to abrasion through excessive movement between bone and implant. For this reason, plastic hip joint sockets have been embedded in a ring or bowl of metal or ceramic which, in turn, can be firmly jointed to a bone by accretion and/or ingrowth of tissue, for example as described in German Patent No. 2411617 and U.S. Pat. No. 3,840,904. However, apart from the fact that the abrasion causing wear now occurs at the interface between the metal bowl and plastic implant, this solution of the problem has the disadvantage that the elasticity of the implant relative to the bone is lost.

Accordingly, it is an object of the invention to provide a plastic implant in which the wear due to movements relative to the bone is prevented to a large extent without unduly impairing the elasticity of the plastic implant.

It is another object of the invention to provide a bone implant of a plastic body which is provided with a contact surface having increased wear resistance.

Briefly, the invention provides a bone implant made of a plastic body which defines a contact surface for contacting a bone and a metal grid embedded in and exposed to the contact surface of the body in order to impart an increased wear resistance to the contact surface relative to a bone.

The plastic body may be made, for example of polyethylene and may be shaped, for use as a hip joint socket. The metal grid is made of a metal, for example, selected from the group consisting of titanium and titanium alloys. In addition, the metal grid is preferably formed as a wire mesh. The structure of the metal grid is such as to have little effect on the elasticity of the implant body. To this end, the cross sections of the ridges (i.e. crests) and the wires can always be selected so that they do not unduly stiffen the implant.

The grid reinforcement drastically reduces the contact surface between the plastic body and the bone so that possible abrasion is considerably diminished. In addition, the embedded wire grid greatly increases the wear resistance of the surface or contact area of the plastic implant which is in contact with the bone.

Because the ridges of the metal grid are at least partially surrounded by plastic, that is, by being embedded in the plastic, relative movements between the metal grid and plastic body are avoided.

The embedment of the metal grid in the contact surface of the plastic body may be performed with a relatively simple technique. For example, the plastic body may be softened at an elevated temperature and the metal grid may be pressed into the plastic body under elevated pressure. The increase in temperature of the plastic body is limited to temperatures below the crystallite melting temperature, i.e. 135° C.–140° C. The required pressure for embedding the wire grid depends on the structure of the grid and on the chosen temperature. For example the pressure may be up to four kiloponds per square millimeter (4 kp/mm$^2$).

Accretion and ingrowth of tissue can be promoted especially if several layers of an anchoring structure are applied to the embedded metal grid. In this case, each layer is made as a porous layer from metal wire with the pores of each layer being of increasing size from layer-to-layer in a direction away from the contact surface of the plastic body. In this regard, it has been found to be appropriate, especially for wire mesh if the ridges form an enlarged bearing surface. This enlargement of the ridges can be achieved, for example, by rolling the layers before or after stacking of the individual layers. For mutual adhesion, the porous layers, as well as the embedded metal grid, are advantageously subjected to a sintering process (diffusion welding) after stacking of the porous layers on the metal grid so that a metallurgical bond is formed at least in the local partial regions where the grid and layers are in contact.

Figure 2:
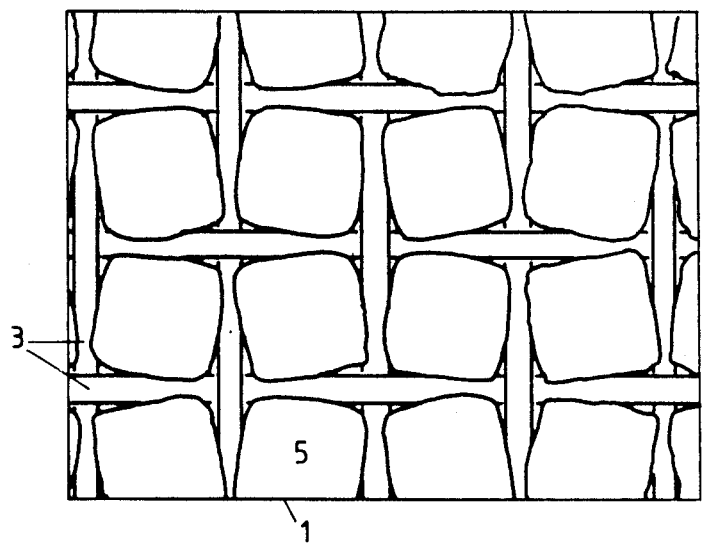

These and other objects and advantages of the invention will become more apparent from the following detailed description taken in conjunction with the accompanying drawings wherein:

FIG. 1 illustrates a cross section through an implant surface constructed in accordance with the invention; and FIG. 2 illustrates a top view of a plastic body having a metal grid embedded therein.

Referring to FIG. 1, the bone implant which is used, for example, as a hip joint socket, is made of a plastic body, for example of polyethylene and has a contact surface for contacting a bone, such as a pelvic bone. In addition, a metal grid 2 is embedded in the surface of the plastic body 1. As indicated, the metal grid 2 consists of a wire mesh of individual metal wires 3. As further indicated in FIG. 1, the summit regions, i.e. crests 4 of the grid protrude slightly from the contact surface 5 of the implant 1 so as to be exposed to the contact surface 5 in order to impart an increased wear resistance to the surface 5 relative to a bone.

Referring to FIG. 2, the surface area of contact of the plastic body 1 relative to a bone (not shown) is considerably decreased since the crests 4 of the wires 3 are exposed.

The grid 2 is made of metal wires which have a diameter and a mesh width, for example, between 0.2 and 1.5 millimeters.

Referring to FIG. 1, the bone implant is also provided with a plurality of porous layers of metal wire which form a support 6. As indicated, the support 6 is made up of three layers 7a, 7b, 7c. Each of these porous layers have pores which are of increasing size from layer-to-layer in a direction away from the contact surface 5. For example with each layer formed of wire mesh, the innermost layer 7c is formed of wires of a diameter of 0.1 millimeters with a mesh width of 0.2 millimeters. The middle layer 7b is formed of wires of a diameter of 0.25 millimeters with a mesh width of 0.5 millimeters. The outermost layer 7a is formed of wires of a diameter of 0.5 millimeters with a mesh width of 1 millimeter. The increasing pore size from the inside layer 7c to the outer layer 7a thus avoids any reduction in pore size in the middle layer 7b.

The support layers 7a, 7b, 7c may be made of metals which are known to be especially tissue-friendly, such as titanium, tantalum, niobium, zirconium or alloys of these metals as base materials or other implant alloys. The layers 7a, 7b, 7c thus form a tissue-friendly surface structure into which bone tissue may grow in the course of time so that the implant is anchored in the bone firmly and without bone cement. Of note, the mesh width of the innermost layer 7c is so narrow that no tissue will grow therethrough. This layer 7c, therefore, forms a complete shield and separation between the bone and the plastic subject to abrasion.

As indicated in FIG. 1, the layers 7a, 7b, 7c are secured to each other with the innermost layer 7c being secured to the metal grid 2 which is embedded in the plastic body 1. Contact may be effected by means of a sintering process so that a metallurgical bond is formed at the various contact points between the surfaces of the layer 7a, 7b, 7c and the grid 2.

The invention thus provides a plastic bone implant with a reinforced wear surface without any impairment of the elasticity of the plastic implant body.

Further, the invention provides a relatively simple structure for reinforcing the contact surface of the plastic implant body.

Figure 3:
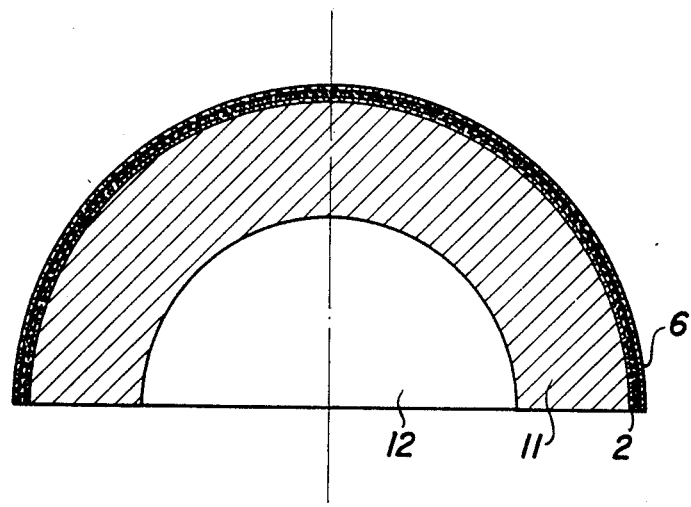

FIG. 3 illustrates diagrammatically an artificial hip joint socket for anchoring in a pelvic bone (not shown), especially in a cement-free manner. The socket body 11 has an internal socket bowl of hemispherical shape for receiving a joint head of a femur prosthesis (not shown); in the surface of contact relative to the bone of the plastic body 11 is embedded a metal grid 2 as shown in FIG. 1. A support 6 consisting of a plurality of porous metal layers is secured to said grid 2 as shown in and described in connection with FIG. 1.

What is claimed is:

1. A bone implant having a plastic body defining a contact surface for contacting a bone, a metal grid embedded in and exposed to said surface of said body to impart an increased wear resistance to said surface relative to a bone and a plurality of porous layers of metal wire secured to said metal grid and extending over said contact surface, said porous layers having pores of increasing size from layer-to-layer in a direction away from said contact surface.

2. A bone implant as set forth in claim 1 wherein said metal grid is formed of crossing wires with at least some of said wires having crests defining enlarged bearing areas.

3. A bone implant as set forth in claim 1 wherein said grid is formed of wire as a diameter of from 0.2 to 1.5 millimeters.

4. A bone implant as set forth in claim 1 wherein said body is made of polyethylene.

5. A bone implant as set forth in claim 1 wherein said metal grid is made of a metal selected from the group consisting of titanium and titanium alloys.

* * * * *

UNITED STATES PATENT AND TRADEMARK OFFICE
CERTIFICATE OF CORRECTION

PATENT NO. : 4,978,355

DATED : December 18, 1990

INVENTOR(S) : OTTO FREY, et al

It is certified that error appears in the above-identified patent and that said Letters Patent is hereby corrected as shown below:

Column 4, line 22 change "wire as" to -wires of-

Signed and Sealed this

Twenty-eighth Day of July, 1992

*Attest:*

DOUGLAS B. COMER

*Attesting Officer*  Acting Commissioner of Patents and Trademarks